United States Patent [19]

Slattery et al.

[11] 4,137,256

[45] Jan. 30, 1979

[54] PREPARATION OF PERACETIC ACID BY OXIDATION OF ACETALDEHYDE

[75] Inventors: Gerald H. Slattery, Pasadena, Md.; Leonard Seglin, New York, N.Y.

[73] Assignee: FMC Corporation, Philadelphia, Pa.

[21] Appl. No.: 654,953

[22] Filed: Feb. 3, 1976

Related U.S. Application Data

[63] Continuation of Ser. No. 764,079, Oct. 1, 1968, abandoned.

[51] Int. Cl.² .............................................. C07C 179/12
[52] U.S. Cl. ................................................. 260/502 A
[58] Field of Search ............... 260/502 A, 502 R, 502; 23/284 X

[56] References Cited

U.S. PATENT DOCUMENTS

| 2,314,385 | 3/1943 | Bludworth et al. ............. 260/502 A |
| 3,192,256 | 6/1965 | Maclean ............................ 260/502 A |

FOREIGN PATENT DOCUMENTS

| 678327 | 1/1964 | Canada ................................. 260/502 A |
| 1149243 | 4/1969 | United Kingdom ................ 260/502 A |

OTHER PUBLICATIONS

Batten, "Chem. Abstract," vol. 73 (1970), p. 36865g.

*Primary Examiner*—James O. Thomas, Jr.
*Assistant Examiner*—W. B. Lone
*Attorney, Agent, or Firm*—Charles C. Fellows; Frank Ianno

[57] ABSTRACT

This specification discloses a vapor phase process for oxidizing acetaldehyde to peracetic acid, acetic acid being also formed at the same time, in an elongated reaction zone into which oxygen is fed through a plurality of oxygen injection sites spaced along the length of the reaction zone. The reaction gas mixture velocity through the reaction zone in the areas of the oxygen injection sites is maintained in excess of the flame velocity of the reaction gas mixture and the reaction zone temperature is maintained between about 140° C. and about 180° C.

8 Claims, 3 Drawing Figures

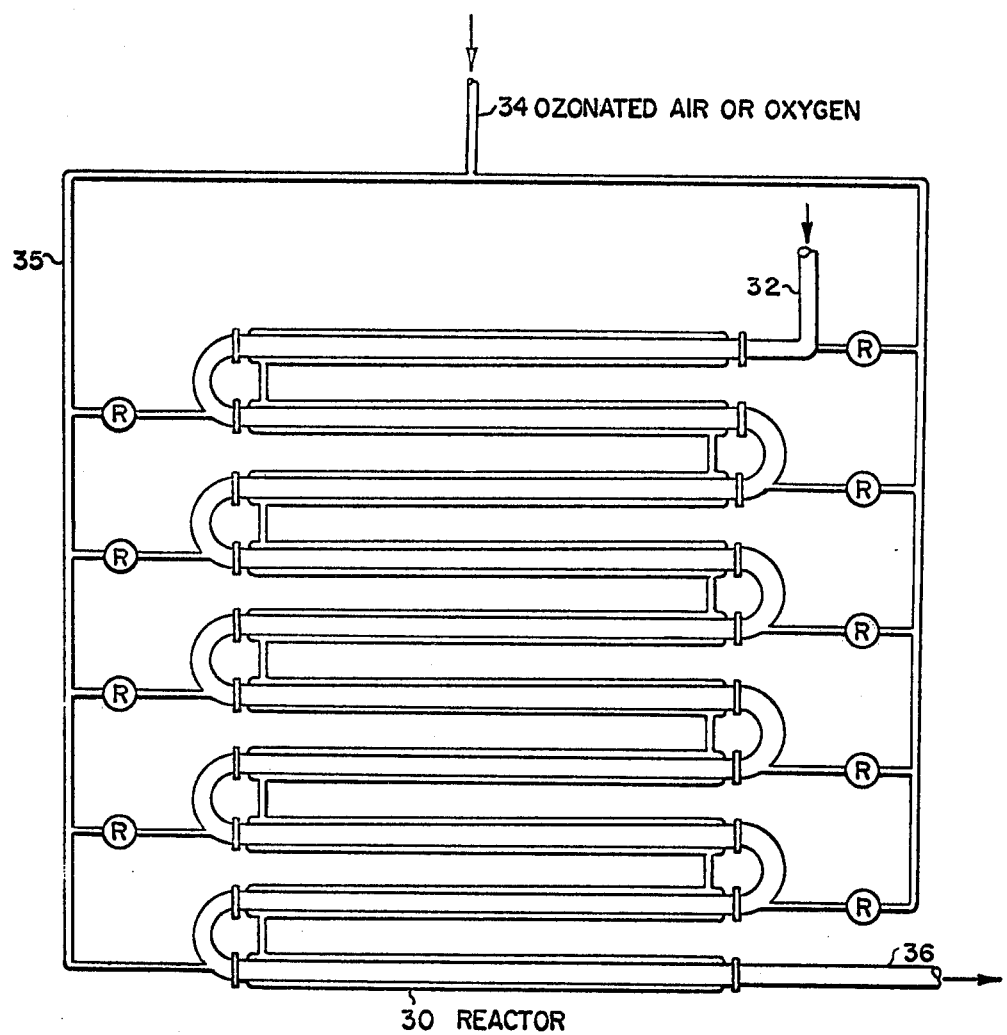

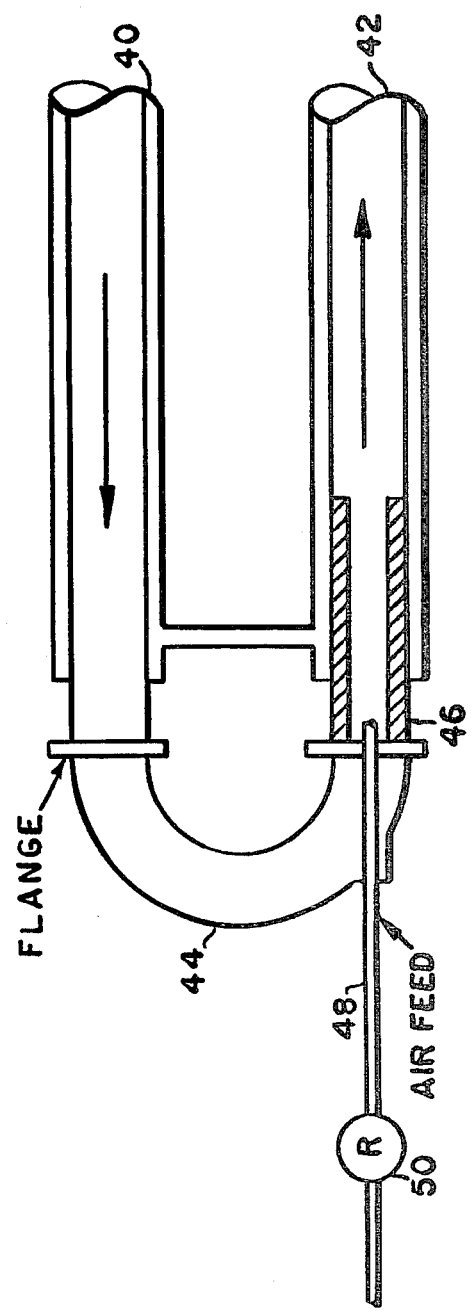

PREPARATION OF PERACETIC ACID BY OXIDATION OF ACETALDEHYDE

This is a continuation of application Ser. No. 764,079, filed Oct. 1, 1968, now abandoned.

BACKGROUND OF THE INVENTION

1. Field of the Invention

This invention relates to the vapor phase oxidation of acetaldehyde to peracetic acid, acetic acid being also formed at the same time.

2. Description of the Prior Art

A vapor phase process for producing peracetic acid by reacting acetaldehyde with oxygen at up to 232° C. and pressures up to 50 pounds per square inch was disclosed by Bludworth in U.S. Pat. No. 2,314,383, Mar. 23, 1943. More recently it has been suggested to feed acetaldehyde and oxygen to a heated aluminum reactor and pass the gaseous reaction products to a fractionating column to rapidly separate peracetic acid from unreacted acetaldehyde and acetic acid.

The known vapor phase reactors contain, as an essential element, a fan, blower or other stirrer capable of creating vigorous mixing throughout the entire reactor volume. This type of reactor, used by Bludworth and others, is properly termed a steady-state backmix flow reactor.

Bludworth disclosed producing 6.65 parts of peracetic acid by weight per minute or 400 parts per hour while recycling through the backmix blower, in the reactor loop, 170 parts per minute or 10,000 parts per hour of hot reaction gases. To produce 400 pounds of product peracetic acid per hour required recycling over 5 tons of hot recycle gases per hour against pressure and within the confines of a reactor loop. The blower employed in such a process obviously has to be large and efficient. Blower failure in these fan-type, back-mix, reactors results in an explosion which is the reason why the vapor phase process has not been used commercially. A successful blower has to be large and capable of withstanding an explosion which makes the blower economically undesirable in terms high initial cost and expense of operation.

Though the theoretical stoichiometric ratio of acetaldehyde to oxygen in the vapor phase process is 1:1, Bludworth disclosed acetaldehyde to oxygen ratios of at least 8:1. British Pat. No. 927,053, published 20 years after Bludworth, May 22, 1963, claimed an improved overall acetaldehyde to oxygen ratio of about 5 to 1. This British patent divided the Bludworth reaction between two reactors, the first reactor containing as "an essential element an efficient fan or blower capable of creating vigorous mixing throughout the entire reactor volume".

It is the principal object of this invention to provide a vapor phase process for oxidizing acetaldehyde to peracetic acid that can be operated without using a steady-state back-mix flow reactor, and which can use low acetaldehyde to oxygen ratios so costs are minimized, and in which danger of explosion is reduced to an acceptable level.

SUMMARY OF THE INVENTION

We have now discovered a vapor phase process for oxidizing acetaldehyde to peracetic acid in an elongated reaction zone, preferably a tubular reactor, free of fans, blowers, stirrers or other back-mixing devices, and employing low over-all acetaldehyde to oxygen ratios, preferably in the range of 2:1 to 3:1. The process comprises feeding vaporous acetaldehyde acid into a tubular reactor, maintained at about 140° to 180° C. The oxygen is fed to the reactor, preferably as an oxygen gas mixture such as air, at a plurality of injection sites, preferably at least three, located along the reactor length. The reactor is designed and the feed rate of acetaldehyde and oxygen selected so that the reaction gas velocity in the zones of the oxygen or oxygen-gas injection sites in the reactor exceeds the flame velocity of the acetaldehyde-oxygen or oxygen gas mixture in these zones.

The oxygen fed to the reactor preferably, but not necessarily, contains a small amount, up to 2% by weight based on oxygen, of ozone.

The acetaldehyde feed rate can be varied over a wide range, however, the preferred feed rates are 10 to 50 pounds per hour of vaporous acetaldehyde per cubic foot of total reactor volume.

The process enjoys the advantage of simple reactor design free of fans or blowers, i.e., a steady-state plug flow reactor; moreover, acetaldehyde to oxygen ratios of lower than 1:1 can be used if desired, though this is not a preferred ratio of the process. Additionally, inexpensive tubular reactors of metal pipe may be used.

BRIEF DESCRIPTION OF THE DRAWINGS

FIG. 2 is a diagram of the aluminum pipe reactor used in Example 1.

FIG. 3 is a diagram showing the details of the air injection section of the modified reactor used in Example 3.

DESCRIPTION OF THE INVENTION AND THE PREFERRED EMBODIMENTS

Figure 1:
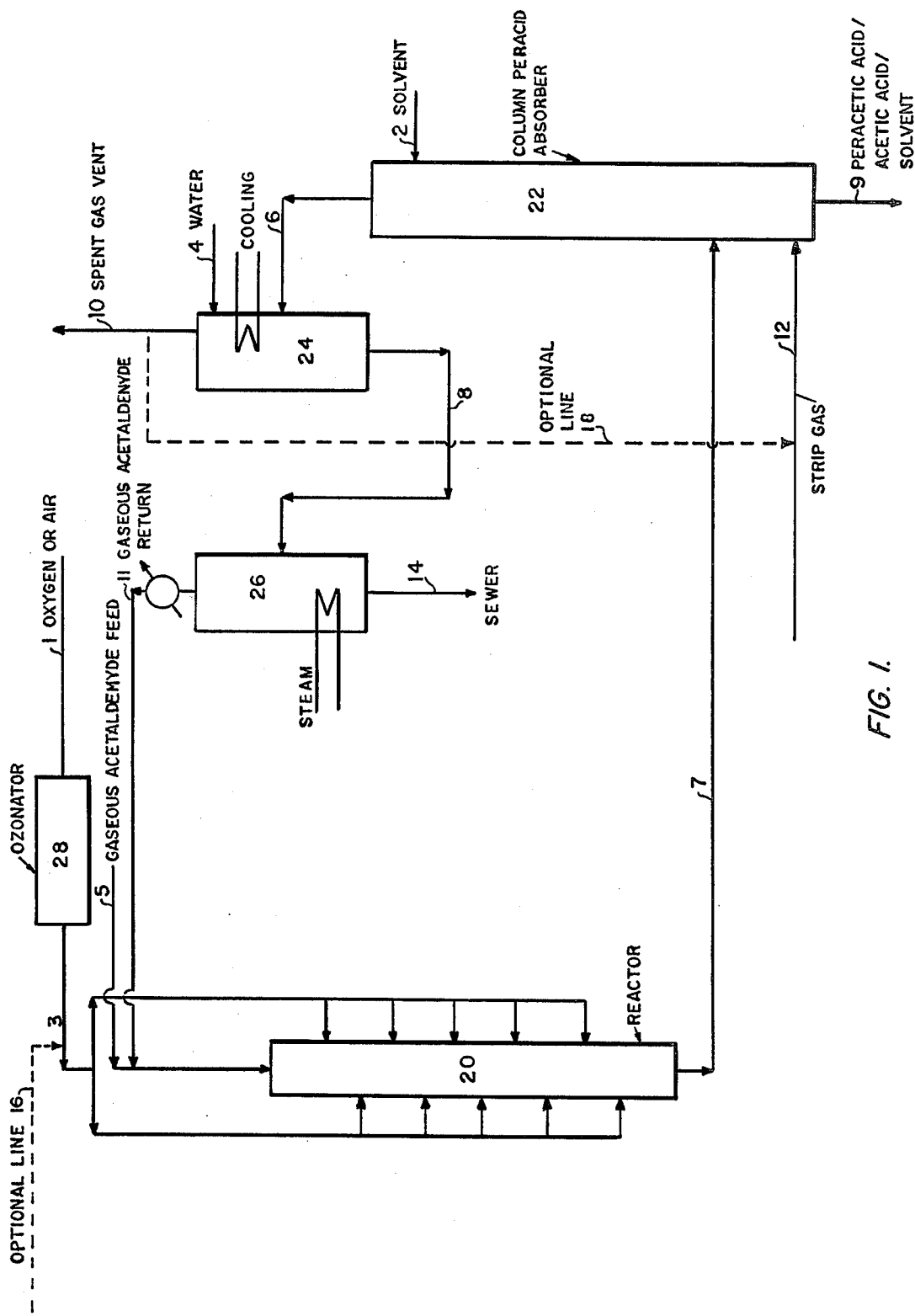
FIG. 1 is a block flow diagram of the overall process for producing and recovering peracetic acid.

Improved yields of peracetic acid formed by the vapor phase oxidation of acetaldehyde are obtained by using an inert tubular reactor designed to permit introduction of oxygen or an oxygen-gas mixture at a plurality of sites along the reactor length, and maintaining reaction gas mixture velocities in the oxygen-injection zones of the reactor that exceed the flame velocities of the corresponding reaction gas mixtures. The critical reaction gas mixture velocity can be achieved by feeding the reacting gases at a rate such that the critical velocity is exceeded throughout the entire reactor. Alternately, the reactor, in the zones of the oxygen or oxygen-gas injection sites, hereinafter referred to as the air injection sites, may be designed to speed the flow of the reaction gases through these zones at velocities in excess of the flame velocity of the reaction gas mixtures. The reactor-gas velocity does not have to exceed the flame velocity throughout the entire reactor, once the initial high velocity mixing of the reactants has been accomplished.

Any surface inert to the reaction products which does not catalyze the decomposition of peracetic acid to acetic acid can be used in a reactor. We prefer reactors made of cleaned glass or cleaned aluminum, and most preferably tubular aluminum. We have used tubular aluminum reactors made from aluminum tubing which was formed into a coil which was immersed in a controlled temperature bath, and lengths of jacketed aluminum pipe connected in series.

It is advisable, although not absolutely necessary, to treat aluminum reactors so that the surface does not cause conversion of peracetic acid to acetic acid. For example, an aluminum reactor can be picked with a 5% nitric acid solution.

As the number of air injection sites are increased along the reactor length, the peracetic acid production rate in pounds per hour per cubic foot of reactor volume increases. For example, when using ozonated air as the oxygen source we have varied the number of air injection sites from 1 to 10 in a reactor composed of ten, 20-foot sections of jacketed one and one-half inch diameter Schedule 40, aluminum pipe, connected in series. We found that as the number of air injection sites was increased from one through ten, the peracetic acid production rate, in pounds per hour per cubic foot of reactor volume, increased from about 3.8 pounds per hour per cubic foot for one air injection site to 6.7 pounds per hour per cubic foot for ten air injection sites when about 33 pounds of acetaldehyde per hour was vaporized and fed to the reactor and the acetaldehyde to oxygen ratio was about 2.7:1. The results obtained indicated that when all other conditions are held constant, more air injection sites will further increase the reactor productivity for this particular reactor, possibly to ten pounds per hour per cubic foot of reactor volume with an infinite number of air injection sites.

Acetaldehyde conversions of up to 50% of the acetaldehyde per pass can be obtained; however, conversions of 20 to 30% are preferred to maximize yields. High acetaldehyde conversions, of 40 to 50%, are accompanied by relatively high by-product formation, thus lowering overall process efficiencies. When using the reactor described in Example 3, a 20% conversion gives about a 95% efficiency, a 30% conversion gives about an 88% efficiency, and a 40% conversion gives only about a 65% efficiency.

The reactors may be operated so that the overall reaction gas velocities through the reactor exceeds the reaction gas mixture flame velocity. A more convenient method of having sufficient reactor volume and developing the necessary high reaction gas velocities in the areas of the air injection sites is to have the air injection sections of the reactor somewhat smaller than the general reactor diameter. This speeds up the gas flow through these critical zones, and permits the use of reasonable size reactor tubes which provide good cubic volume in which the reaction can occur. Using the 10 tube pipe reactor described in Example 1, ozonated air, atmospheric pressure, and gas velocities of about 10 feet per second in the first tube to 16 feet per second in the last tube (the overall velocity increase being due to the addition of air in each tube), the oxidation of acetaldehyde to peracetic acid proceeded smoothly, without fires and explosions. However, when the reactor was operated under a pressure of 7–10 pounds per square inch of gauge pressure, all other operating conditions being the same, the increased pressure slowed the velocity of the reaction gases from the 10 to 16 feet per second range at atmospheric pressure to a 7 to 11 feet per second range at the increased pressure; after a stable reaction period of about an hour the reactor became unstable, and fires and explosions began to occur in some of the tubes. Restricting the size of the tubes, from 1½ inches in diameter to ¾ of an inch in diameter for a length of only 8 inches in the oxygen gas injection sections of these tubes, increased the reaction gas velocity by a factor of about four (to 21 feet per second in the first tube to about 50 feet per second in the last tube). This reaction gas velocity exceeded the flame velocity in the critical oxygen injection zones and thus controlled the reaction.

The reaction is controlled by feeding the oxygen or oxygen-gas mixture into the reactor at three or more injection sites and maintaining the reaction gas mixture velocity in the injection zones in excess of the reaction gas mixture flame velocity. When the reaction gas velocities exceed their flame velocities a momentary flame or explosion would be extinguished or blown out by the fast moving gas stream, thus preventing a stable fire in the reactor should ignition occur.

The general process for producing and recovering peracetic acid by the vapor phase oxidation process of this invention is described with reference to FIG. 1. Oxygen or air is continuously fed to ozonator 28 through line 1 and ozonated air leaves through line 3 and is fed to reactor 20 at a plurality of locations. Gaseous acetaldehyde is continuously fed to the reactor through line 5. The reaction gas mixture leaves the reactor through line 7 and is fed to the column peracid absorber 22. The absorbing solvent is fed to column 22 through line 2. Strip gas (nitrogen or other inert gas) is fed to the absorber bottom through line 12 to remove dissolved acetaldehyde. Product peracetic acid, acetic acid and solvent are removed from column 22 through line 9. The overhead gases, containing principally inert gases (nitrogen, carbon dioxide, unreacted oxygen) and acetaldehyde from the top of column 22 are removed through line 6 and fed to absorption tower 24 to which is also fed water to absorb the acetaldehyde. The overhead gases from the absorber tower are removed from the system through line 10, from which a portion of these inert gases may be recycled to the absorber bottom as strip gas through line 12. The acetaldehyde water solution leaves the scrubber through line 8 and is fed to distillation unit 26. The overhead from unit 26, gaseous acetaldehyde, is returned to the reactor through line 11 and water is removed from unit 26 through line 14.

A reactor for use in the general process is described with reference to FIG. 2. The reactor is made of ten 20-foot sections of jacketed, one and one-half inch diameter, Schedule 40, alloy 6061, temper T-6, aluminum pipe, connected in series. The total cubic volume of the reactor is about 2.4 cubic feet. The reactor temperature is maintained by circulating hot water through the jackets and controlling the amount of oxygen fed to each section of the reactor.

Gaseous acetaldehyde is continuously fed to the reactor 30 through line 32. Ozonated air is fed through line 34 to the manifold distributor 35 which feeds air to each tube of the reactor. A rotameter is used to control the amount of air fed to each tube of reactor 30. The reaction gas mixture leaves the reactor through line 36.

Construction details of the air injection sites as generally used in the reactor shown in FIG. 2 are described with reference to FIG. 3. Two of the reactor sections of one and one-half inch aluminum pipe, 40 and 42 are connected by tube turn 44 which carries the air feed line 48. Reactor section 42 contains an aluminum insert 46 which is 8 inches long and has an internal diameter of ¾ of an inch. The air feed line 48 is of such length that it projects 2 inches into the aluminum insert 46. The amount of air fed through line 48 is controlled by rotameter 50. The reaction gas mixture flows from line 40 through tube turn 44. As the gas goes from tube turn 44 through insert 46 its velocity speeds up due to the restriction. A controlled amount of air is added through feed line 48 to the reaction gas mixture passing through insert 46.

The flame velocities of a number of reaction gas mixtures were measured. The reactor shown in FIG. 2 was used to make controlled amounts of peracetic acid using an ozonated air supply. The effluent gas from the reactor was passed through a test device, a piece of 1½ inch Schedule 40 aluminum pipe about 10 feet long, equipped to measure the burning rate of the effluent gas from the reactor. The composition of the various mixtures tested were carefully determined. The analyses shown below do not report trace amounts of elements normally found in air, or minor amounts of contaminents, such as carbon dioxide, which can result from the vapor phase oxidation of acetaldehyde to peracetic acid. When the reactor was running under substantially constant conditions and the reactor effluent flow through the test device was stable the gas in the test device was ignited and the flame velocity measured. The effluent gas from the reactor entered the test pipe at a temperature of approximately 140° C. The flame velocities, and analyses of the number of reaction gas mixtures are shown in Table 1.

TABLE 1

FLAME VELOCITY TESTS
Reaction Gas Mixture Composition (Mol %)

| Run No. | Acetaldehyde | Oxygen ($O_2$) | Nitrogen $N_2$ | Peracetic Acid | Flame velocity in Feet/Second |
|---|---|---|---|---|---|
| 1 | 13.4 | 5.9 | 79.5 | 0.9 | No go (1) |
| 2 | 10.9 | 2.7 | 81.4 | 3.6 | No go (1) |
| 3 | 12.7 | 1.4 | 77.9 | 8.1 | 3.6 |
| 4 | 29.0 | 12.3 | 55.5 | 2.7 | 5.2 |
| 5 | 22.2 | 8.2 | 62.0 | 4.9 | 7.1 |
| 6 | 12.2 | 15.3 | 69.1 | 3.1 | 7.5 |
| 7 | 22.7 | 3.1 | 60.4 | 9.8 | 10.5 |
| 8 | 78.4 | 2.8 | 3.5 | 16.2 | 12.3 |
| 9 | 25.2 | 7.0 | 58.4 | 6.4 | 13.7 |
| 10 | 79.3 | 15.9 | 0.9 | 3.5 | 25.1 |
| 11 | 3.8 | 17.7 | 75.8 | 2.5 | 436 |
| 12 | 8.1 | 16.4 | 72.3 | 2.8 | 452 |
| 13 | 52.1 | 40.9 | 0.6 | 5.8 | 972 |
| 14 | 28.8 | 64.8 | 0.9 | 5.5 | 7945 |

(1) Did not burn under the test conditions.

The data clearly show that reaction gas mixtures with high oxygen to acetaldehyde ratios, and low nitrogen levels, when ignited reach sonic and supersonic flame velocities that amount to gas phase detonations (Runs No. 13 and 14). Considering the acetaldehyde and peracetic acid in the reaction gas mixtures as fuel it is apparent that even in the presence of substantial amounts of nitrogen, if the available oxygen greatly exceeds the fuel, very high flame velocities occur (Runs No. 11 and 12). However, a great deal of latitude in operating conditions is available in the use of oxygen or an oxygen gas mixture such as air. In the absence of diluent the reaction can be controlled when using oxygen as the oxidizing gas source if the acetaldehyde and peracetic acid greatly exceed the available oxygen. When there is a substantial amount of nitrogen or other diluent present in the reaction gas mixture, the oxygen to fuel ratio can approach and even exceed 1:1 without developing excessive flame velocities. When very little oxygen is available for the total amount of fuel the gas mixture will not burn.

Runs 8 to 10 show that high ratios of acetaldehyde to oxygen, i.e., fuel to oxygen, can be tolerated in the present process. Effective control can also be assisted by diluting the reaction with a material inert to the reaction. The diluent, though inert to the reaction, can be a fuel which if ignited will burn, rather than a completely inert diluent each as nitrogen. Saturated hydrocarbons such as methane, ethane and the like can be used in place of nitrogen or excess acetaldehyde in helping to control the reaction.

The process operates successfully using at least three oxygen gas injection sites provided the reaction gas velocity exceeds the flame velocity of the reaction gas mixture through the oxygen injection zones of the reactor. However, the overall productivity and conversion attained are generally increased as the number of air injection sites increases for a given reactor when all other reactor conditions are kept constant. The required amount of oxidizing gas can be equally divided among the selected number of gas injection sites or the oxidizing gas may be proportioned in any manner found desirable to maintain favorable reaction conditions. Generally varying the amount of oxidizing gas, usually air, fed to each injection site to maintain the reactor temperature between air injection sites, in the preferred temperature range of 150–170° C. is more beneficial than proportioning the air by some arbitrary system though the practical effect is that about equal amounts of air go to each injection site.

Reaction temperature ranges of about 140° to 180° C. and preferably 150° to 170° C. are used in this process. At these temperatures, when the reaction gas mixture velocities exceed their flame velocities through the oxygen injection zones the residence time in the reactor can be varied from about 7 to 120 seconds with the preferred residence time being 7 to 20 seconds. This amounts to a through put of about 10 to 50 pounds of acetaldehyde per hour per cubic foot of total reactor volume.

Acetaldehyde can be oxidized to peracetic acid according to this process over a wide pressure range. The pressure in the reactor may be as high as theoretical, e.g., 50 atmospheres at 150° C. As the pressure is increased in a reactor, all other conditions being held constant, there is an increase in reactor productivity as there are more pounds of reaction gases in the reactor. However, the increased amount of reaction gases present increases the amount of heat produced in the reactor until the available heat transfer is utilized to capacity and thus limits a further productivity increase. By-product formation also increases as the pressure increases. Hence, we prefer to operate at relatively low pressures. Optimum design suggests just sufficient pressure to produce gas flow through the recovery zone, up to about 20 to 30 psig.

The pressure in the 10 tube reactor of Example 3 was varied from atmospheric pressure up to 20 psia. As the pressure increased, and the other reaction conditions were held constant, the reaction gas velocity through the reactor slowed down and at higher pressures, means had to be taken to maintain the reaction gas velocity through the reactor in the areas of the oxygen injection sites in excess of the reaction gas flame velocity. In this ten tube reactor the reactor pressure affected conversion and acetic acid formation only as the pressure affected reactor residence time.

The following examples, illustrating the novel process disclosed herein are given without any intention that the invention be limited thereto. All parts and percentages are by weight.

EXAMPLE 1

An aluminum reactor consisting of ten 20 foot sections of jacketed one and one-half inch, schedule 40 aluminum pipe, alloy 6061, T-6 (ASTM B241-67) connected in series as shown in FIG. 2, was used. 24.4 Pounds of gaseous acetaldehyde and 347 standard cubic feet of air, containing 2.2 milligrams per liter of ozone, were fed per hour into the reactor. The air was distributed in substantially equal portions to 9 injection sites, each site being located at the beginning of each of the last 9 tubes in a 10 tube reactor. The reactor pressure was maintained at 2 pounds per square inch gauge (psig) and the reactor temperature was maintained at 150° to 170° C. The reaction gas velocity in the area of the gas injection sites ranged from 6 feet per second in the first tube to 16 feet per second in the last tube. No fires or explosions occurred and operating conditions were maintained. Peracetic acid was recovered at the rate of 8.2 pounds per hour. About 68% of the oxygen in the feed air was consumed. About 21% of the acetaldehyde was consumed of which about 92% was converted to peracetic acid.

EXAMPLE 2

Using the reactor of Example 1 and maintaining the conditions of Example 1, the reactor pressure was gradually increased from 2 to 7 psig. The reactor operation was smooth for a short while when the reaction mixture exploded causing several self-extinguishing pops or explosions which ultimately produced stable fire in the reactor which required a shut-down of the reactor. Several additional attempts showed the same results; that is, the reaction proceeded smoothly at 2 psig but became unstable at 7 psig. The increased pressure reduced the gas velocities in the reactor from the 6 and 16 foot per second range in Example 1 to only 4 feet per second in the first tube to 11 feet per second in the last tube at 7 psig. Data obtained in the short period between "pops" showed 92% consumption of the oxygen in the air feed. About 30% of the acetaldehyde was consumed of which 91% was converted to peracetic acid which was produced at the rate of about 11 pounds per hour.

EXAMPLE 3

The reactor of Example 1 was modified by reducing the dimensions of the air injection sites to from about 1½ inches to ¾ inch in diameter; this increased the gas velocity by a factor of 4. The reactor was restarted and acetaldehyde was fed to the reactor at the rate of 23.7 pounds per hour, and air containing 3.9 milligrams of ozone per liter was fed at the rate of 357 scfh, with the air being divided into substantially equal proportions between the 10 tubes. The reactor was started under 2 pounds per square inch gauge pressure. Operation was smooth and trouble free for many hours, and then the pressure was increased to 7 psig for the test run. Subsequent tests showed that the reactor pressure could be increased to 20 psig without encountering reactor instability. Markedly improved reactor stability at 7-20 psig pressure operation, results from the redesign of the air injection sites which increased the gas velocity by a factor of about 4, from 4-11 feet per second at 7 psig to 21-50 feet per second at 7 psig in the air injection zones. Peracetic acid was produced at the rate of 9.2 pounds per hour. About 79% of the oxygen in the air feed was consumed. About 25% of the acetaldehyde was consumed of which about 89% was converted to peracetic acid.

EXAMPLE 4

The modified aluminum reactor of Example 3 was fed 35.1 pounds per hour of vaporized acetaldehyde. Ozonated air containing 3.0 milligrams per liter of ozone was fed at the rate of 519 scfh to the reactor through 10 injection sites, each site being located at the beginning of each of the reactor tubes. The reactor pressure was maintained at 10 psig and the reactor gas temperature was maintained at 150°-170° C. by pressure controlled steam in the tube jackets. The reaction proceeded smoothly over 4 hours with the reactor effluent gases passing to an absorber column where 15.9 pounds per hour of peracetic acid were recovered while the unreacted acetaldehyde and non-condensable gases were removed overhead for subsequent recovery. About 88% of the oxygen in the feed air was consumed. About 28% of the acetaldehyde was consumed of which about 90% was converted to peracetic acid. The reactor space productivity was 6.7 pounds per hour per cubic foot of reactor volume. The residence time was approximately 20 seconds. The tubes, in the areas of the air injection sites, were about ¾ of an inch in diameter and 8 inches long. The reaction gas velocity in the air injection zones was about 20 feet per second in the first tube increasing in each tube to about 50 feet per second in the last tube.

EXAMPLE 5

Example 4 was repeated, varying only the number of air injection sites, but keeping the total reactor volume constant and all the other operating conditions substantially the same. The effect on reactor space rate productivity obtained by varying the number of air injection sites is shown in Table 2. Production rate and reactor productivity are very significantly affected by the number of air injection sites in that reactor productivity is increased 80% by increasing the number of air injection sites from 1 to 10 with all other reaction conditions being kept the same.

TABLE 2

| Run No. | 1 | 2 | 3 | 4 |
|---|---|---|---|---|
| Reactor Pressure PSIG | 10.5 | 10.5 | 10.5 | 10.5 |
| Acetaldehyde Feed Rate lb/hr | 35.1 | 35.1 | 35.1 | 35.1 |
| Air SCFH | 519 | 516 | 518 | 509 |
| Ozone (O$_3$) mg/l | 3.0 | 2.6 | 2.6 | 2.6 |
| Mol Ratio acetaldehyde/oxygen (O$_2$) | 2.8 | 2.8 | 2.8 | 2.8 |
| Peracetic Acid Produced lb/hr | 15.9 | 12.8 | 10.8 | 8.9 |
| Space Rate Productivity lb/hr/cu.ft. | 6.7 | 5.4 | 4.6 | 3.8 |
| No. of air injection sites | 10 | 5 | 3 | 1 |

EXAMPLE 6

Example 4 was repeated except that only the last nine sites were used and the second air injection site was the only site utilized to inject ozonated air into the reactor (the first air injection site was not used). The air injection site in the second tube was fed with 98.5 scfh of ozonated air feed which contained 15.5 milligrams of ozone per standard filter of air. Additional (unozonated) air at the rate of 451 scfh was divided about equally among air injection sites 3 through 10. The space rate productivity adjusted for nine tubes only dropped about 10%, thus permitting separate handling of ozonated versus unozonated air at a small price in productivity loss. This permits economy in air handling as the air must be very dry for efficient ozonation using a corona type ozonator. Dry air is fed to the reactor but it does not have to be as dry as the air which is ozonated.

EXAMPLE 7

Example 4 was repeated but varying the pressure in the reactor from 2½ to 20 pounds per square inch gauge. The reaction feed rates, ozone levels, reactor temperatures including both the control temperature level and the peak temperature level recorded, the peracetic acid production rate in pounds per hour and the space rate productivity are included in Table 3.

Table 3

| Run No. | 1 | 2 | 3 | 4 |
|---|---|---|---|---|
| Reactor Pressure PSIG | 2.5 | 7.0 | 15.0 | 20.0 |
| Acetaldehyde Feed Rate lb/hr | 24.6 | 28 | 46.1 | 25.4 |
| Air SCFH | 355 | 443 | 707 | 547 |
| Ozone ($O_3$) mg/l | 3.5 | 3.5 | 2.1 | 2.6 |
| Mol Ratio Acetaldehyde/oxygen ($O_2$) | 2.7 | 2.6 | 2.7 | 2.0 |
| Temperature C° | 146 | 146 | 143 | 146 |
| Peracetic Acid Produced lb/hr | 8.9 | 11.0 | 18.8 | 15.6 |
| Space Rate Productivity lb/hr/cu.ft. | 3.8 | 4.6 | 8.0 | 6.5 |
| No. of Tubes | 10 | 10 | 10 | 10 |

EXAMPLE 8

Example 4 was repeated at 2.0 pounds per square inch gauge pressure using oxygen containing 8 milligrams per liter of ozone in place of air as the oxidizing gas. Vaporous acetaldehyde was fed to the reactor at the rate of 54 pounds per hour while ozonated oxygen containing 8 milligrams of ozone per liter was fed at the rate of 100 standard cubic feet per hour to a ten tube reactor. The control temperature was set at 146° C. and a peak temperature in the tubes of 154° C. was recorded. Peracetic acid was produced at the rate of 16.6 pounds per hour with a space productivity rate of 7.0 pounds per cubic foot per hour.

As will be apparent to those skilled in the art, numerous modifications and variations of the process illustrated above may be made without departing from the spirit of the invention within the scope of the following claims.

What is claimed is:

1. In the vapor phase process for oxidizing acetaldehyde to peracetic acid, acetic acid being formed at the same time, in an elongated reaction zone maintained at a temperature between 140° C. and 180° C., the improvement which comprises introducing acetaldehyde into a steady-plate plug-flow reactor while introducing an oxygen containing gas selected from the group consisting of air and oxygen into the reactor at a plurality of at least three oxygen injection sites spaced along the reactor in the direction of travel of the reaction mixture and maintaining reaction gas velocities through the reaction zone in the areas of the oxygen injection sites in excess of the flame velocity of the reaction gas mixture of between 5.2 and 452 feet per second.

2. The process of claim 1 in which vaporous acetaldehyde is fed to the reaction zone at the rate of 10 to 50 pounds per hour per cubic foot of total reactor volume.

3. The process of claim 1 in which the plug-flow reactor is constructed of tubular aluminum.

4. The process of claim 1 in which the acetaldehyde to oxygen ratios are in the range of 2:1 to 3:1.

5. The process of claim 1 in which oxygen is introduced into the reaction zone in a mixture with an inert diluent.

6. The process of claim 1 in which up to 2% by weight of the oxygen is ozone.

7. The process of claim 1 in which three to ten oxygen injection sites spaced along the plug-flow reactor are employed.

8. The process of claim 1 in which the reaction gas velocities in the areas of the gas injection sites is maintained between 10 and 50 feet per second.

* * * * *

UNITED STATES PATENT AND TRADEMARK OFFICE
CERTIFICATE OF CORRECTION

PATENT NO. : 4,137,256
DATED : 30 January 1979
INVENTOR(S) : Gerald H. Slattery and Leonard Seglin It is certified that error appears in the above-identified patent and that said Letters Patent are hereby corrected as shown below:

Column 3, line 1, "picked" should read --pickled--.
Column 5, line 67, "each" should read --such--.
Column 8, line 64, "filter" should read --liter--.

Signed and Sealed this

Twelfth Day of June 1979

[SEAL]

Attest:

RUTH C. MASON
Attesting Officer

DONALD W. BANNER
Commissioner of Patents and Trademarks